United States Patent [19]

Levy et al.

[11] Patent Number: 4,584,722
[45] Date of Patent: Apr. 29, 1986

[54] PROSTHETIC TENDON

[75] Inventors: Moshe Levy; Shaul A. Gassner, both of Rehovot; Reuben Farber, Givataim, all of Israel

[73] Assignee: Yeda Research and Development Co., Ltd., Rehovot, Israel

[21] Appl. No.: 493,327

[22] Filed: May 10, 1983

[30] Foreign Application Priority Data

May 24, 1982 [IL] Israel ........................................ 65855

[51] Int. Cl.$^4$ .............................................. A61F 1/00
[52] U.S. Cl. ..................................... 623/13; 128/92 C
[58] Field of Search ...................... 128/335, 334, 92 C, 128/92 G, 22 R; 3/1, 1.4, 1.9, 1.91

[56] References Cited

U.S. PATENT DOCUMENTS

| | | | |
|---|---|---|---|
| 2,978,787 | 4/1961 | Liebig | 3/1.4 |
| 3,276,448 | 10/1966 | Kronenthal | 3/1.4 |
| 3,463,158 | 8/1969 | Schmitt et al. | 3/1 |
| 3,613,120 | 10/1971 | McFarland | 3/1 |
| 4,060,081 | 11/1977 | Yannas et al. | 128/DIG. 8 |
| 4,149,277 | 4/1979 | Bokros | 3/1 |
| 4,187,558 | 2/1980 | Dahlen et al. | 3/1 |

FOREIGN PATENT DOCUMENTS

| | | | |
|---|---|---|---|
| 708000 | 4/1965 | Canada | 3/1 |
| 2221112 | 11/1972 | Fed. Rep. of Germany | 3/1 |

Primary Examiner—Richard J. Apley
Assistant Examiner—David J. Isabella
Attorney, Agent, or Firm—Browdy and Neimark

[57] ABSTRACT

There is provided a tendon prosthesis comprising in combination an essentially tubular core of physiologically acceptable and mechanically strong fabric, embedded in a flexible polymer, which member is provided with a surrounding woven sleeve of a biodegradable fabric, said inner fabric core being exposed at both ends for attachment to the bone and muscle, and a process for the production of same which comprises stretching a knitted dacron strip to form an elliptical cross-section member, longitudinally open, embedding it in polymerizable silicon monomer, polymerizing same, weaving around same a sleeve from biodegradable filaments, and closing the sleeve at the two ends around exposed dacron core.

13 Claims, 11 Drawing Figures

PROSTHETIC TENDON

FIELD OF THE INVENTION

There is provided a tendon prosthesis with a biodegradable sleeve, a process for the production of same and its use in prosthesis in human and veterinary medicine.

BACKGROUND OF THE INVENTION

The repair of damaged tendons, especially in the palm of the hand, as well as in other locations, causes severe problems. The conventional method of implantation of tendons in cases of severe injuries of the hand requires three surgical operations, namely, the implantation of a silicon rod; its removal after a period of about six weeks; and the insertion into the thus created tunnel of a tendon taken from a donor site of the body. In cases of attachment to a finger, there is created a "window" in the finger bone and inserting the end of the tendon into same, connecting it by means of a stainless steel wire which is tied to a button on the other side of the bone. The suture of flexor tendons in the palm of the hand, in the region called "no man's land" is often functionally unsuccessful due to adhesions of the tendon to neighboring tissues. This is the reason why substitution of a torn tendon by a new one is generally resorted to. In cases of destruction of tendons, these are replaced by donor tendons from other body sites or by prosthetic tendons. One of the more serious problems of prosthetic tendons (hereinafter PT), is their adhesion to surrounding tissues.

It is one of the objects of the present invention to overcome this problem, and to provide PT which are mechanically strong, can be implanted in one step, and which do not cause problems of adhesion.

SUMMARY OF THE INVENTION

There are provided prosthetic tendons (PT) which are implanted in a one-step surgical procedure, and which fulfill all the phsyiological requirements, without problems of adhesion to surrounding tissues, and which are provided with means for attachment to the bone (like finger phalanges) and other bones and to the muscle. There is also provided a process for the production of such PTs.

The novel prosthetic tendon comprises a core of a polymer fabric on which was cast a layer of silicon rubber or the like, which provides elasticity and a smooth movement of the tendon, said core of fabric and silicon rubber being encased in a sleeve of a biodegradable material. The sleeve is preferably a woven one, which provides adequate elasticity, and prevents the growth of surrounding tissue towards the silicon rubber. After being in place for a certain period of time, the said exterior sleeve undergoes enzymatic degradation and disappears. It thus serves as temporary spacer between the tendon and its surroundings, and the surrounding tissue subsequently develops into a tendon sheath which will be remote from the surface of the silicon rubber. The prosthetic member is provided with novel means of attachment to the bone.

There is also provided a method of production of such PT which comprises molding a core of suitable polymer, such as silicon rubber containing a strong synthetic fabric, and weaving on same a sleeve of a biodegradable material, and sealing same at its ends, to prevent unravelling and its sliding on the silicon core.

Advantageously, the PT is provided at one of its ends with means for attachment to a bone. According to a preferred embodiment, a rectangular elongated strip of Dacron or similar fabric of surgical grade, is tensioned, thus imparting to it a traverse section of open elliptical shape. There is provided a mold into which a polymerizable material is introduced, into which the said elliptical core is inserted, and which is polymerized, resulting in a layer of said polymer around said inner core. At this stage a sleeve of a biodegradable material is woven from fibers thereof. Good results were obtained by the use of 16 filaments of a polymer of polyglycolic acid (PGA), of the formula

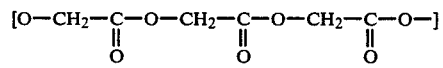

which were woven to provide a tightly fitting sleeve, the ends of which were sealed by applying an elevated temperature of about 240° C. The outer sleeve and the enclosed silicon are terminated at a point before the insertions points, thus the two ends of the PT are of a smaller diameter than that of the main part of the PT. To one of the ends of the PT there is attached a member made of an inert metal, such as stainless steel of surgical grade, which is in the shape of an open cylinder surrounding the end of the PT, which is passed through a hole drilled in the bone to which the PT is to be attached, and which, after passage through said hole, is bent at a 90° angle to be flush with said bone, firmly anchoring the said end of the PT in place.

The PT is surgically implanted at one end in muscle, and during several weeks there takes place an ingrowth of fibrocytes and connective tissue into the pores of the Dacron fabric from each end, resulting in a biological bond between the PT and muscles. At the place where the PT is connected with the bone, the inner fabric remains exposed to permit ingrowth of bone tissue into said fabric, at which stage the said tendon is held in place by the said metal anchor. After this period of time, the material of the biodegradable sleeve undergoes degradation by the enzymes attacking it, and it gradually disappears, leaving a new tendon within the silicon layer, which is remote from the surrounding tissue.

The invention is illustrated with reference to the enclosed schematical drawings, which are not according to scale, and in which.

Figure 5:
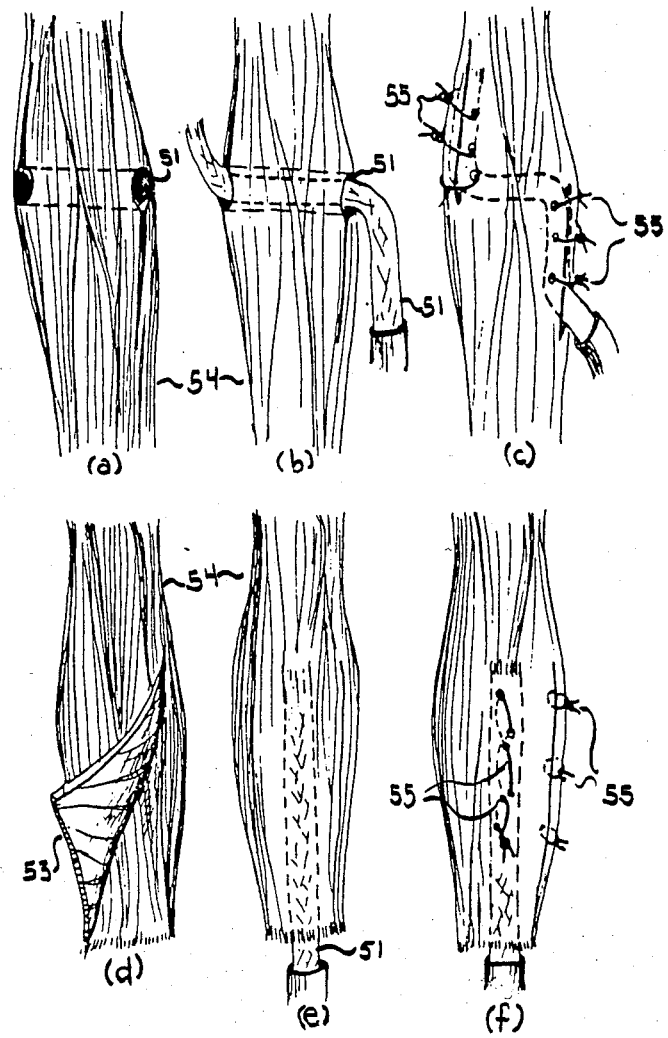
Figure 6:
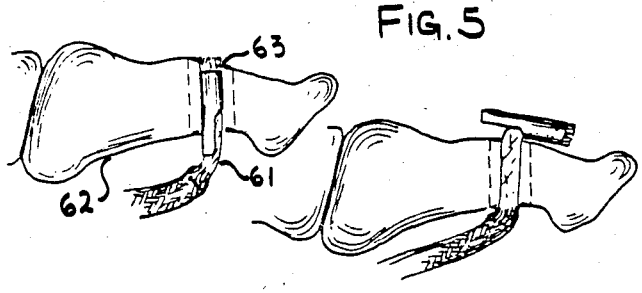

FIG. 5 (a), (b), (c), (d), (e) and (f) illustrates the insertion of such prosthesis in muscle; and FIG. 6 illustrates the insertion and anchoring of the prosthesis in bone.

DESCRIPTION OF THE PREFERRED EMBODIMENT

The prosthetic tendon (PT) has as backbone a strip of Dacron (Meadox Double Velour Dacron Fabric, Cat # 019136) Dacron is a registered trademark for a polyester made from polyethylene terephthalate. The Dacron backbone strip has a width of about 7 mm width is cut to the desired length. A typical length is from 50 to about 150 mm. The strip is tensioned, and this imparts to it an open elliptical cross-section. There is provided a mold of adequate length and of elliptical cross-section, consisting of two half sections. The Dacron tube (open at its length) is introduced into a half mold which there has been previously introduced a quantity of silicon (Dow-Corning Sylgard 186 Silicon Elastomer). While the strip is maintained under tension by two holders, and the second part of the mold is filled with the same silicon, both portions of the resin being admixed with Sylgard 186 curing agent (1:10), after which the mold is closed and the silicon polymerized after removal of air by vacuum at 110° C. during 20 minutes. The mold is cooled, and the PT removed. Around the Darcon fabric there is thus provided a silicon coating, and around this there is woven a sleeve consisting of 16 filaments of polyglycolic acid (Davis and Geck 2/0 Dexon). The cross section of the complete PT is elliptical, about 3 mm width and about 1 mm height. The Dacron is exposed at both ends of the strand, and the outer sleeve is firmly closed around the Dacron core by application of heat of about 240° C., fusing the outer sleeve filaments.

The polymer from which the sleeve is made is biodegradable, and due to enzymatic degradation it disappears after a certain period of time.

Figure 1:
FIG. 1 is a perspective view of the anchor in open state.
Figure 2:
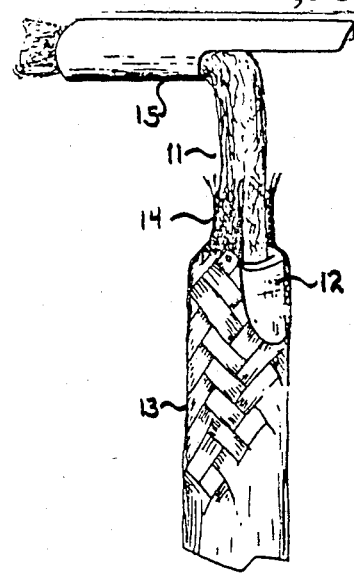
FIG. 2 is a perspective view of part of a prosthesis of the invention with attached anchor.
Figure 3:
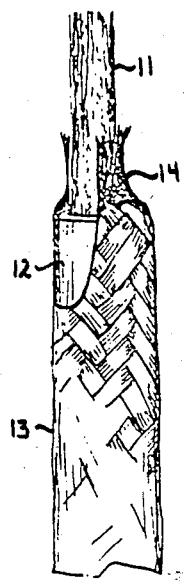
FIG. 3 illustrates the sealing of the outer sleeve at its point of termination.
Figure 4:
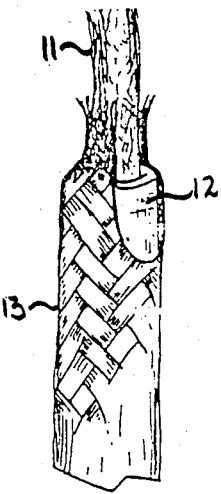
FIG. 4 shows part of the prosthesis, in partial section.

As shown in FIGS. 2, 3, and 4, the prosthesis consists of an inner core of Darcon ribbon, in open elliptical form, 11, around which there is provided a layer of silicon 12, and which is provided with a sleeve 13 of biodegradable material, which sleeve is closed around the Dacron core at both ends, as shown at 14. For anchoring to a bone, there is provided a stainless steel member 15, shown in FIG. 1 and FIG. 2. This anchor is made from a tubular profile with a longitudinal opening. The Dacron fiber is inserted into the tubular member, and this is firmly attached to same by application of mechanical force. When the prosthetic tendon is to be attached to a bone, like a finger phalanx, a small hole is bored through same, slightly larger than the diameter of the tubular anchor, which is passed therethrough while being coaxial with the main portion of the tendon. After passage through the hole, the anchor is bent by 90° and thus anchored firmly in place as shown in FIG. 6 where the anchor 15 is shown during the passage stage and after being bent over. As shown in FIG. 5, the exposed Dacron core 51 is passed, via a hole 52 or flap 53, into the muscle 54, and sutured to it as shown in FIG. 5(c) and FIG. 5(f) by stitches 55. During some weeks there occurs an ingrowth of fibrocytes and connective tissue into this fabric and a biological bond is established. FIG. 6 illustrates the attachment of the exposed Dacron fabric 61 to bone 62 by insertion into a hole 63. The anchor illustrated with reference to FIG. 6 is of about 0.5 mm diameter, and the hole needs to be slightly larger. When bent over, a T-formed anchor is formed.

The PGA sleeve disappears after some weeks, and this sleeve prevents the adhesion of the surrounding tissue to the silicon tendon. It acts as spacer and isolater, and after its disappearance there results a tendon sheath surrounding the implant and remote from it. The rupture load was measured by an Instron device and was found to be about 10.400 Kg for the tendon, with elongation of 57%. The rupture load of the anchor-Dacron junction is about 2.5 Kg. Experiments carried out on turkeys showed that the tendon prosthesis of the invention fulfills all the physiological requirements, and preliminary experiments with humans confirm this.

Tendons of varying lengths (40, 70, 110 and 150 mm length) were produced and tested. All gave satisfactory results.

It is clear that the above description is by way of illustration only and that various modifications in the nature of the materials used and in the dimensions and arrangements of parts may be resorted to without departing from the scope and spirit of the invention.

We claim:

1. A tendon prosthesis consisting essentially of a tubular core of biocompatible fabric, embedded in a polymer which provides elasticity and prevents tissue ingrowth therethrough, said core being encased in a sleeve of biodegradable material, said biodegradable material being selected so as to prevent growth of surrounding tissue towards said core, and said core having fabric extending beyond said sleeve at both ends for attachment to the bone and muscle, whereby upon implantation the sleeve undergoes enzymatic degradation thus serving as a temporary spacer between the newly developed tendon sheath and the surface of the core structure.

2. A tendon prosthesis according to claim 1, wherein the inner core is an elliptical open tubular member of polyester fabric made from polyethylene terephthalate, which is embedded in silicon rubber, the outer sleeve being woven from filaments of polyglycolic acid (PGA).

3. A tendon prosthesis according to claim 1, further including a tubular anchor with a longitudinal opening, attached to the exposed fabric of said core extending beyond said sleeve, and adapted to pass through a hole in the bone and to be bent over to attach it firmly to the bone.

4. A tendon prosthesis according to claim 1, wherein said biocompatible fabric is composed of polyester fibers made from polyethylene terephthalate and said polymer is a silicon polymer, and wherein said core is the product of stretching a strip of said fabric of about 7 mm width, embedded in silicon polymer, so as to form an elliptical member having a major axis of about 3 mm and a minor axis of about 1 mm.

5. A tendon prosthesis according to claim 1, wherein said outer sleeve is closed around the inner fabric of said core at both ends of the prosthesis.

6. A tendon prosthesis in accordance with claim 1, wherein said biodegradable sleeve material is polyglycolic acid.

7. A tendon prosthesis in accordance with claim 1, wherein said biodegradable sleeve is woven.

8. A tendon prosthesis in accordance with claim 6, wherein said biodegradable sleeve is woven.

9. A tendon prosthesis in accordance with claim 1, wherein said core comprises a polyester fabric made from polyethylene terephthalate embedded in silicon polymer.

10. A process for producing a tendon prosthesis consisting essentially of a tubular core of biocompatible fabric, embedded in a polymer which provides elasticity and prevents tissue ingrowth therethrough, said core being encased in a sleeve of biodegradable material, said biodegradable material being selected so as to prevent growth of surrounding tissue towards said core, and said core having fabric extending beyond said sleeve at both ends for attachment to the bone and muscle, comprising stretching a knitted strip of biodegradable fabric to form a longitudinally open elliptical cross-section member, embedding said member in a polymerizable monomer which upon polymerization becomes a polymer which provides elasticity and prevents tissue ingrowth therethrough, polymerizing said monomer, weaving around said polymer a sleeve from filaments of said biodegradable material, and closing the sleeve at the two ends around the exposed fabric core.

11. A process according to claim 10, where an anchor is attached to one of the ends of the exposed fabric core.

12. A process in accordance with claim 10, wherein said biocompatible fabric comprises a polyester fabric made from polyethylene terephthalate and said polymer comprises a silicon polymer.

13. A process according to claim 12, wherein and anchor is attached to one of the ends of the exposed fabric core.

* * * * *